United States Patent [19]
Yun et al.

[11] Patent Number: 5,621,162
[45] Date of Patent: Apr. 15, 1997

[54] GAS SENSOR FOR DETECTING GASES GENERATED FROM FOOD PRODUCTS

[75] Inventors: Dong H. Yun, Anyang-si; Chul H. Kwon, Seoul; Kyuchung Lee, Seoul; Hyeon S. Park, Seoul; Hyung K. Hong; Hyun W. Shin, both of Kwacheon-si; Sung T. Kim, Seoul, all of Rep. of Korea

[73] Assignee: LG Semicon Co., Ltd., Chungcheongbuk-do, Rep. of Korea

[21] Appl. No.: 590,299

[22] Filed: Jan. 23, 1996

[30] Foreign Application Priority Data

Jan. 24, 1995 [KR] Rep. of Korea ............... 1178/1995

[51] Int. Cl.$^6$ ................... G01N 31/00; G01N 27/12
[52] U.S. Cl. ................ 73/23.34; 73/23.2; 73/31.06
[58] Field of Search ................ 73/23.2, 23.34, 73/23.3, 31.06

[56] References Cited

U.S. PATENT DOCUMENTS

| | | | |
|---|---|---|---|
| 4,381,922 | 5/1983 | Frey et al. | 422/98 |
| 4,457,161 | 7/1984 | Iwanaga et al. | 73/23 |
| 4,502,321 | 3/1985 | Zuckerman | 73/23 |
| 4,520,651 | 6/1985 | Litman | 73/23 |
| 4,770,027 | 9/1988 | Ehara et al. | 73/23 |
| 4,794,323 | 12/1988 | Zhou et al. | 324/71.5 |
| 4,885,929 | 12/1989 | Kasahara et al. | 73/23 |
| 4,893,108 | 1/1990 | Kolesar, Jr. et al. | 338/34 |
| 5,178,744 | 1/1993 | Nakazawa et al. | 204/425 |
| 5,222,388 | 6/1993 | Sinha et al. | 73/23.2 |
| 5,223,783 | 6/1993 | Wilis | 324/71.5 |
| 5,407,743 | 4/1995 | Clough et al. | 428/357 |
| 5,448,906 | 9/1995 | Cheung | 73/31.06 |

FOREIGN PATENT DOCUMENTS 3103761  4/1991  Japan.

*Primary Examiner*—Hezron E. Williams
*Assistant Examiner*—J. David Wiggins
*Attorney, Agent, or Firm*—Morgan, Lewis and Bockius LLP

[57] ABSTRACT

A gas sensor for detecting a gas component from a food item includes a sensing layer having an electrical resistance value that varies in accordance with the concentration and type of the gas component generated from the food item to thereby sense the gas component, first and second electrodes coupled across the sensing layer and connected to a power supply, a heater for heating the gas sensor to a temperature of sensing operation, and a switch connected to an adjustable voltage supply for controlling whether the heater is operated in a first temperature range or in a second temperature range. The sensing layer includes a mixture of $SnO_2$ and $WO_3$ in a predetermined ratio.

9 Claims, 5 Drawing Sheets plan view bottom end view section view

GAS SENSOR FOR DETECTING GASES GENERATED FROM FOOD PRODUCTS

BACKGROUND OF THE INVENTION

1. Field of the Invention

The present invention relates to a gas sensor, and more particularly to a gas sensor for sensing fruits or vegetables and a method of manufacturing the same.

2. Discussion of the Related Art

An effective sensor for sensing an inherent smell component of food (such as fruits and vegetables) is yet to be developed. Among the sensors in existence, the sensitivity for sensing the inherent smell component of the food had been too low to sense fruits and vegetables being put into or out of a container. Already-developed sensors merely sense the gas produced when the food (fruits and vegetables) decays or its freshness degrades.

Generally, when vegetables such as radish, Welsh onion, carrot, or lettuce are put in a storage compartment, the vegetables produce reducing gases, such as sulfuretted hydrogen ($H_2S$), methyl-mercaptan ($CH_3SH$), dimethyl-sulfide (($CH_3)_2S$), and dimethyl-disulfide (($CH_3)_2S_2$), as the storage time grows.

If the vegetables are stored for a long time as described above, the sulfuric compound gases (reducing gases) are generated due to the degraded freshness. Thus, these gases are bonded with oxygen ions adsorbed on the surface of the gas sensor to generate conducting electrons as in the following reaction formula, thereby changing an electric conductivity on the surface of a sensing layer of the gas sensor:

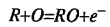

$$R+O=RO+e^-$$

Since the reaction of this formula is active in the vicinity of a metal catalyst on the surface of a sensing layer of the gas sensor, it is very important as to which catalyst of a certain component is added and how much is added. Conventionally, a palladium (Pd) catalyst of 1 wt % is added, and $SnO_2$ is utilized as the sensing layer.

The above-mentioned conventional gas sensor for sensing gases produced due to the degraded freshness from prolonged storage will be described with reference to accompanying drawings. FIGS. 1a–1c is a view showing a structure of a conventional gas sensor for sensing the freshness of food, and FIG. 2 shows a process of manufacturing the gas sensor for sensing the freshness of food.

In manufacturing a gas sensor for sensing the freshness of the food, $SnO_2$ powder is adequately mixed with Pd powder, which is finely ground to be subjected to a heat treatment at 700° C. for about 5 hours. Then, the heat-treated powder mixture is finely ground further, and mixed with an organic material consisting of ethyl-cellulose and alpha-terpinol to create a paste. The mixture in the paste is coated to have a proper size and thickness on an electrode plane of alumina substrate 1 formed with electrodes 2 and a heater 3 via a screen printing method, thereby forming a sensing layer 4.

Thereafter, a drying process is performed; the gas sensor is sintered at 600° C. for 10 minutes; a lead wire is attached; and a packaging process is performed. Thus, the gas sensor is completed.

FIGS. 1a–1c illustrate a situation where the heater is formed on the bottom plane. FIG. 3 is a circuit diagram for showing the operation of the conventional gas sensor. An operation of the conventional gas sensor for sensing the freshness of the food is carried out as follows.

The gas sensor reacts with the sulfuric compound to change electric conductivity. At this time, a resistance variation Rm is supplied to a microprocessor 5 as a voltage variation value in accordance with a resistance dividing ratio with a fixed resistor $R_L$.

In this operation, microprocessor 5 compares the input voltage value with a pre-programmed value to determine the freshness of the vegetables in the storage compartment. Then, once the freshness begins degrading, the rate of freshness degradation is maximally retarded by a temperature control, a humidity control, a pressure control, a quantity control of oxygen/ozone, a quantity control of an anion, etc.

However, the conventional gas sensor and the freshness maintaining apparatus for using the same have the following problems. First, the conventional gas sensor which senses the freshness of the food, such as fruits and vegetables, has low sensitivity in sensing the inherent smell component of the fruits and vegetables, so that it is not distinguishable whether the fruits or vegetables are being put into or being put out from the storing compartment. Moreover, since the putting in or putting out of the fruits and vegetables cannot be distinguished, it is controlled by recognizing that the food, such as the fruits or vegetables, in the storage compartment is as good despite the fact that there is no food in the storing compartment. Consequently, the power consumed by a refrigerator is unnecessarily increased.

SUMMARY OF THE INVENTION

Accordingly, the present invention is directed to a gas sensor and a manufacturing method thereof that substantially obviates one or more of the problems due to limitations and disadvantages of the related art.

An object of the present invention is the provision of a gas sensor capable of sensing a gas component produced from a specific food (such as fruits and vegetables) when the food is put into a food storing apparatus.

Another object of the present invention is the provision of a gas sensor for sensing gases generated from food that has a resistance value in correspondence therewith. Also, electrodes measure a resistance variation of the sensing layer, a heater heats the gas sensor at a sensing operation temperature, and a switch switches a power supply of the heater to allow the heater to be operated in a first temperature range and a second temperature range.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the gas sensor includes a sensor layer for sensing a gas component generated from food, and for varying a resistance value; electrodes for measuring a resistance of the sensing layer; a heater for heating the gas sensor to a temperature of sensing operation; and a switch for controlling whether the heater is operated in a first temperature range or in a second temperature range.

In another aspect, the gas sensor includes a substrate; a heater formed on the substrate for heating the substrate at a sensing operation temperature; first and second electrodes formed on the substrate; a sensor layer formed across the first and second electrodes for sensing a gas component generated from food, and varying a resistance value between the first and second electrodes; and a switch for switching a power supply of the heater to cause the heater to be operated in a first temperature range and a second temperature range.

In a further aspect, the manufacturing method of a gas sensor includes the steps of: preparing a substrate to be used with a heater and electrode; mixing a $SiO_2$ powder with a $WO_3$ powder, finely grinding the resulting to be subjected to a first heat treatment; grinding the first heat treated mixture further, and adding an organic binder and solvent to the resultant material to form a paste; coating the paste on the substrate to form a sensing layer; and performing a second heat treatment, and sintering the resultant structure to perform a packaging process.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENT

Reference will now be made in detail to the preferred embodiments of the present invention, examples of which are illustrated in the accompanying drawings.

Figure 1A:
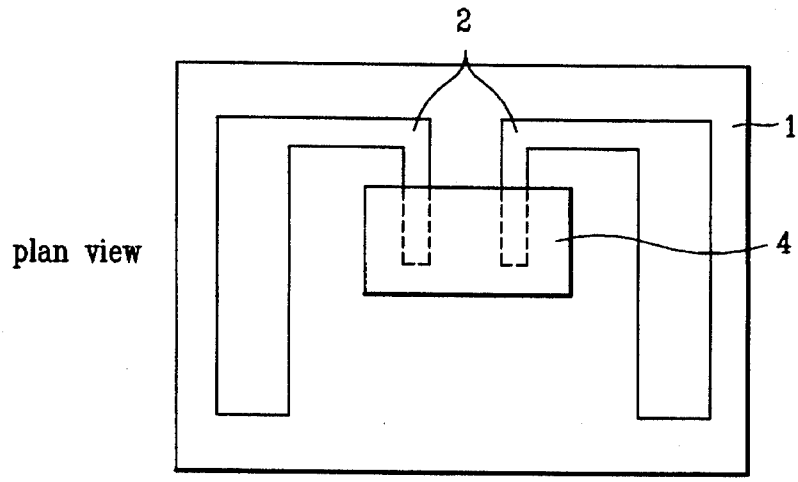
FIGS. 1a–1c show a structure of a conventional gas sensor for sensing the freshness of food.
Figure 1B:
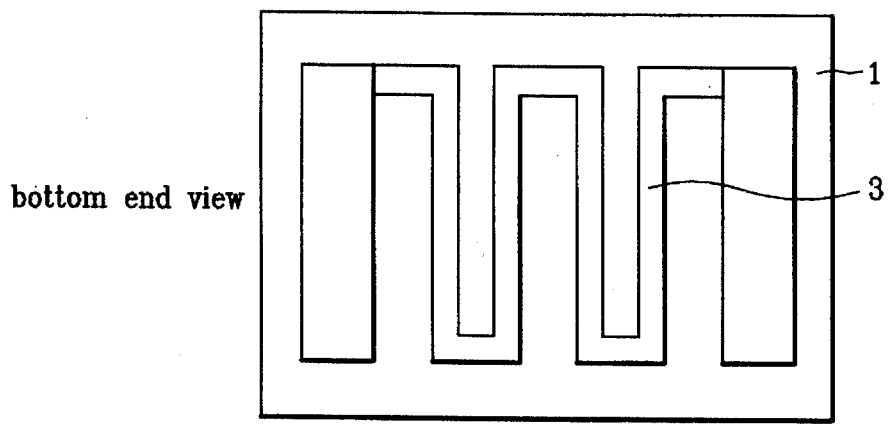
Figure 1C:
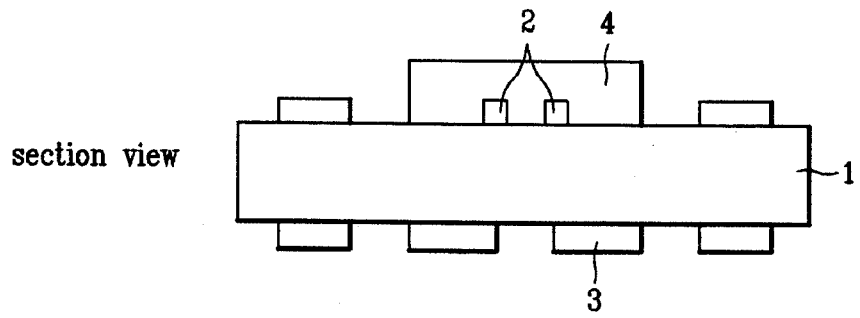
Figure 2:
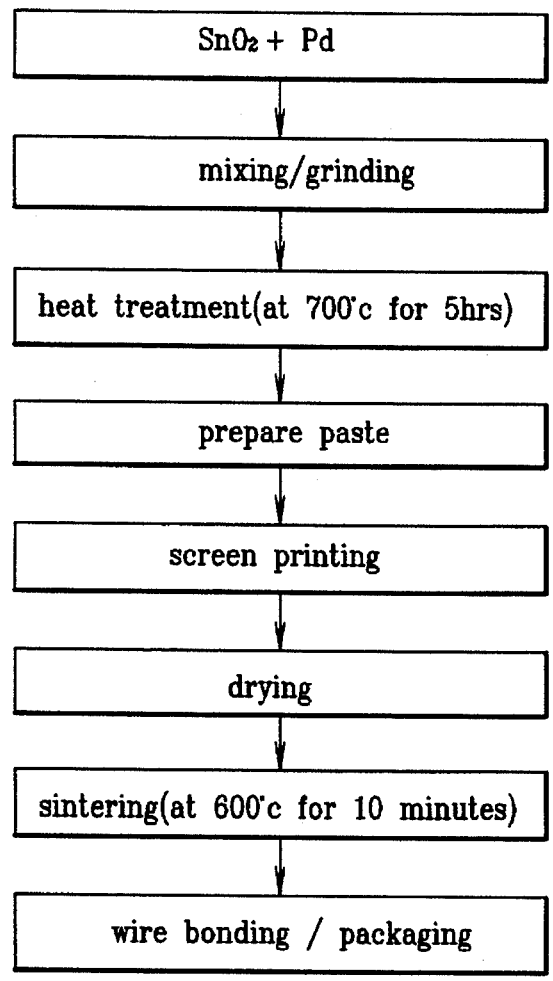
FIG. 2 shows a process of manufacturing the conventional gas sensor for sensing the freshness of food shown in FIGS. 1a–1c.
Figure 3:
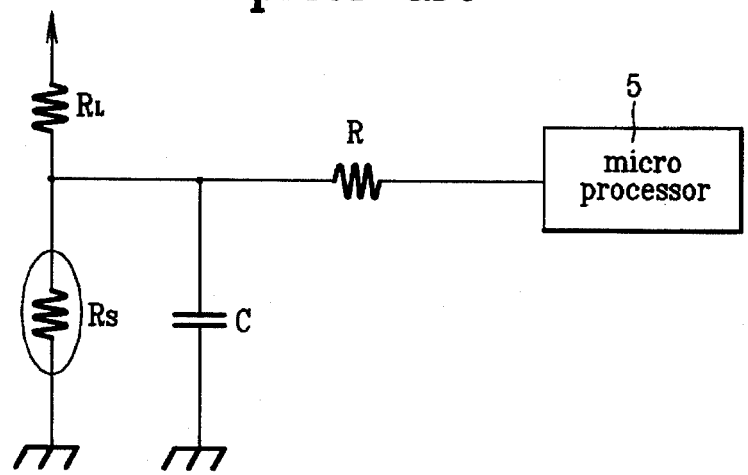
FIG. 3 is a circuit diagram for illustrating an operation of the conventional gas sensor shown in FIGS. 1a–1c.
Figure 4:
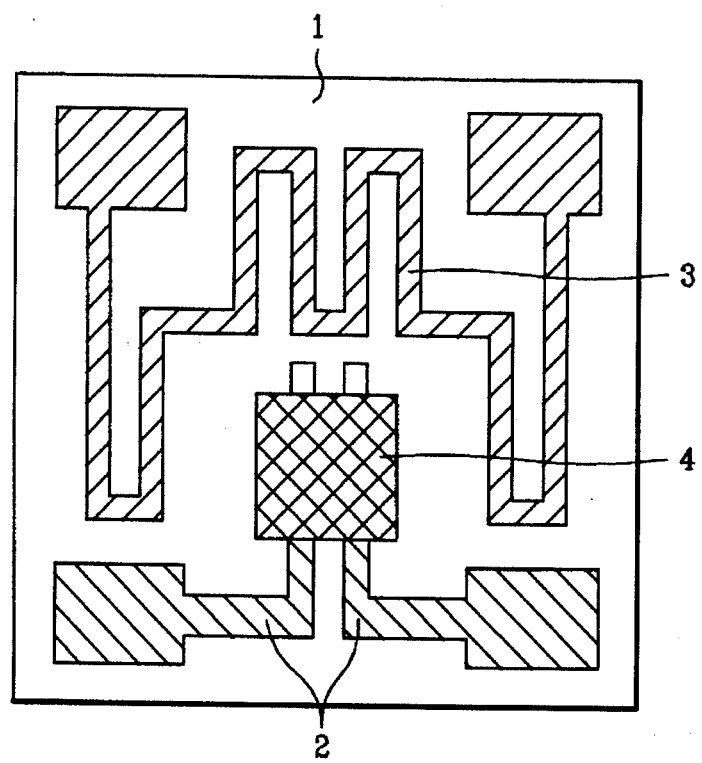
FIG. 4 is a diagram showing a gas sensor according to the present invention.
Figure 5:
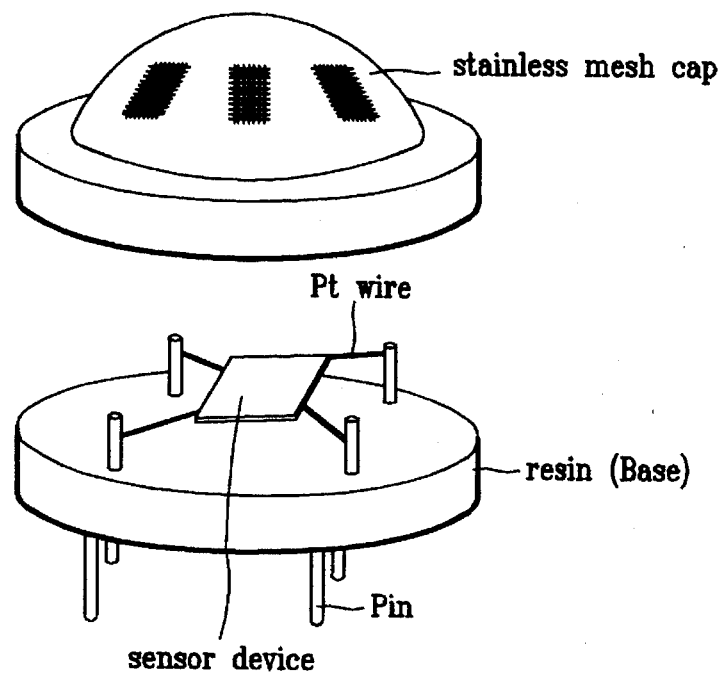
FIG. 5 is a view of assembling the gas sensor according to the present invention.
Figure 6:
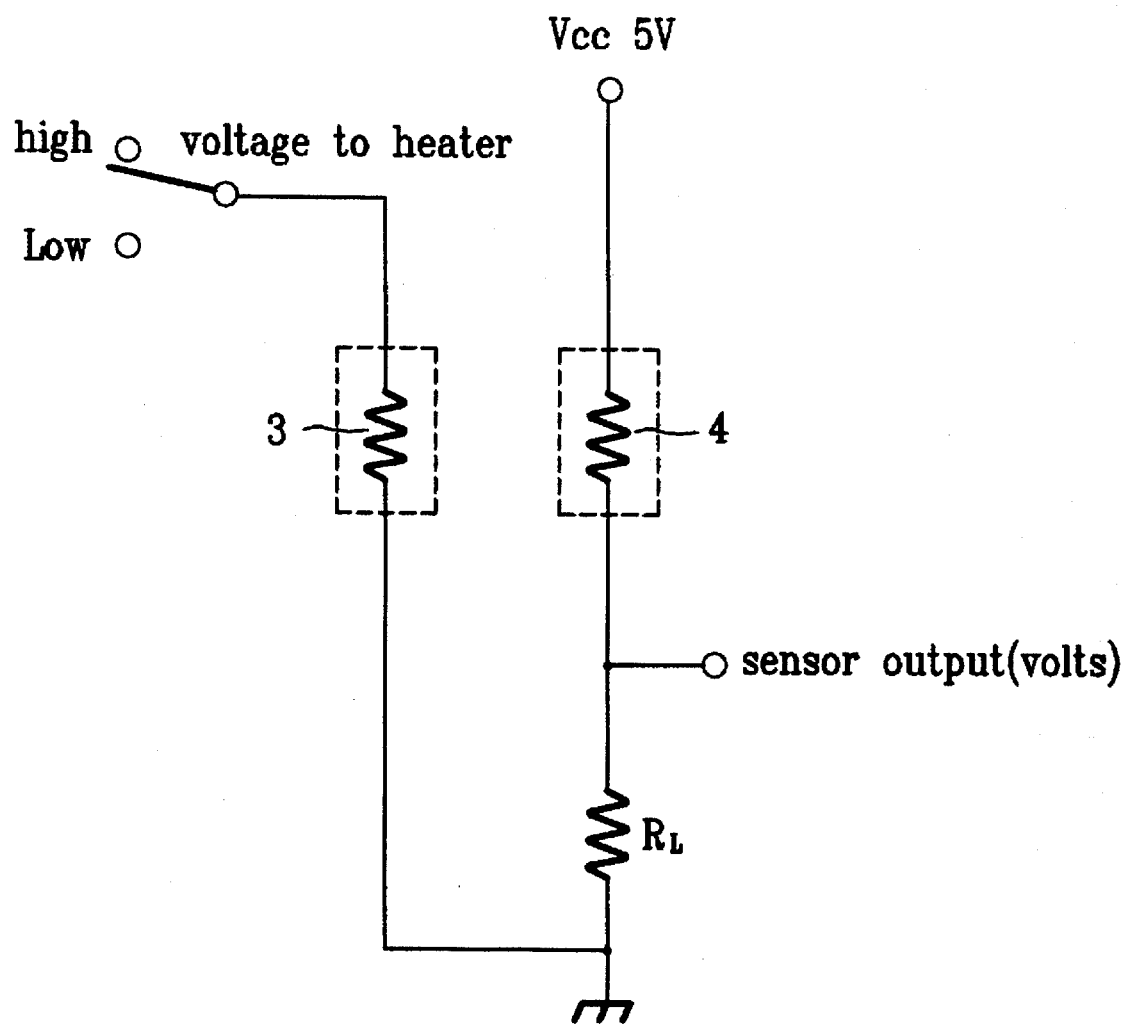
FIG. 6 is an operational circuit diagram showing the gas sensor according to the present invention.

A gas sensor according to the present invention will be described in detail with reference to accompanying drawings. FIG. 4 is a diagram of the gas sensor according to the present invention. FIG. 5 is a view of an assembly of the gas sensor according to the present invention. FIG. 6 is an operation circuit diagram showing the gas sensor according to the present invention.

The gas sensor according to the present invention is constructed such that a heater 3 and electrodes 2 are formed on an alumina substrate 1 spaced from each other by a prescribed distance. A sensing layer 4 for sensing the gas generated by fruits or vegetables is formed on electrodes 2.

At this time, sensing layer 4 is formed for sensing a component of the gas from the fruits or vegetables, wherein the component can be varied and the sensing layer does not require a specific resistance. Thus, sensing layer 4 is formed of a material absolutely different from that of the conventional sensing layer. In order to allow electrodes 2 to measure the varied resistance value of sensing layer 4, sensing layer 4 is formed across the two electrodes 2. Heater 3 is provided for heating substrate 1 so as to permit a temperature of substrate 1 to reach an operational temperature of the gas sensor. The component of sensing layer 4 of the gas sensor according to the present invention is composed of $SnO_2$ and $WO_3$, for example, 80–95 wt % of $SnO_2$ and 5–20 wt % of $WO_3$.

The method of manufacturing the foregoing gas sensor is similar to that of the conventional method, however the composition of sensing layer 4 is different. $SnO_3$ powder is mixed thoroughly with $WO_3$ powder, which is finely ground and subjected to a heat treatment at 500°~800° C. for 4–8 hours.

The thermally-treated powder mixture is further ground, and organic binder and solvent are added thereto for forming a paste suitable for performing a screen printing. The mixture of $SnO_2$ and $WO_3$ in the paste state is coated with a reasonable (effective) thickness and size on the electrode plane of alumina substrate 1 formed with electrodes 2 and heater 3, thereby forming sensing layer 4.

After this, a dry process is performed and the resultant structure is sintered at 500°~800° C. for 1–5 hours. Then, a lead wire is attached and a packaging process is executed to manufacture the gas sensor.

Here, the lead wire sustains the device in the high temperature state and allows electric conduction while minimizing thermal loss. The wire may be formed of Pt, Au, Ag and the like. The wire may have a thickness from several tens of hundreds μm.

The gas sensor according to the present invention may be manufactured and assembled as shown in FIG. 5. Heater 3 is wire-bonded with platinum wires, for example, to two pins of a base supported by a mold resin and electrodes 2 are wire-bonded with platinum wires, for example, to the remaining two pins of four pins which are spaced by a predetermined interval. Then, a meshed cap is assembled while being properly adjusted in a sensor mounting environment. Substrate 1 is supported by the wires.

The gas sensor according to the present invention is operated as follows. FIG. 7 is output waveforms of the gas sensor according to the present invention.

In order to measure a resistance of the sensing layer of the gas sensor according to the present invention, as shown in FIG. 6, an electrostatic voltage Vcc of 5 volts is applied to one electrode 2 of sensing layer 4, and the other electrode 2 is grounded via a resistor $R_L$. One electrode of heater 3 is connected with a switch SW for enabling a voltage supplied to heater 3 to switch from "high voltage" to "low voltage," and vice versa, thereby supplying power to the heater 3. The other electrode is grounded to obtain the voltage across resistor $R_L$ as an output signal. Here, the voltage is adjustably supplied such that heater 3 is operated at high temperature of 250°~350° C. when switch SW is switched to "high" and low temperature of 100°~200° C. when switch SW is switched to "low."

Figure 7A:
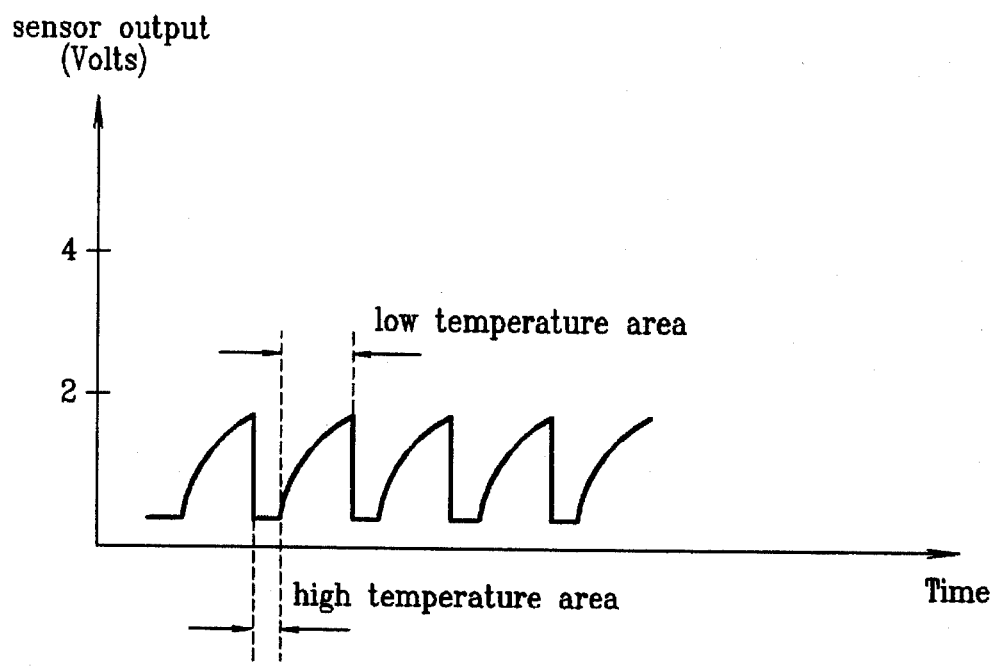
FIGS. 7a and 7b are output waveforms of the gas sensor according to the present invention.

An output waveform in the situation that there is no food (such as the fruits and vegetables) in the storage compartment in the above circuit is as shown in FIG. 7a. That is, when heater 3 is heated at the high temperature, the resistance of sensing layer 4 is relatively high to produce a low output voltage because moisture ($H_2O$) adsorbed on the surface of sensing layer 4 is thoroughly separated and the smell component rarely exists thereabout. If heater 3 is heated at a low temperature, the resistance is slightly decreased from absorbing a small amount of moisture in the atmosphere.

Figure 7B:
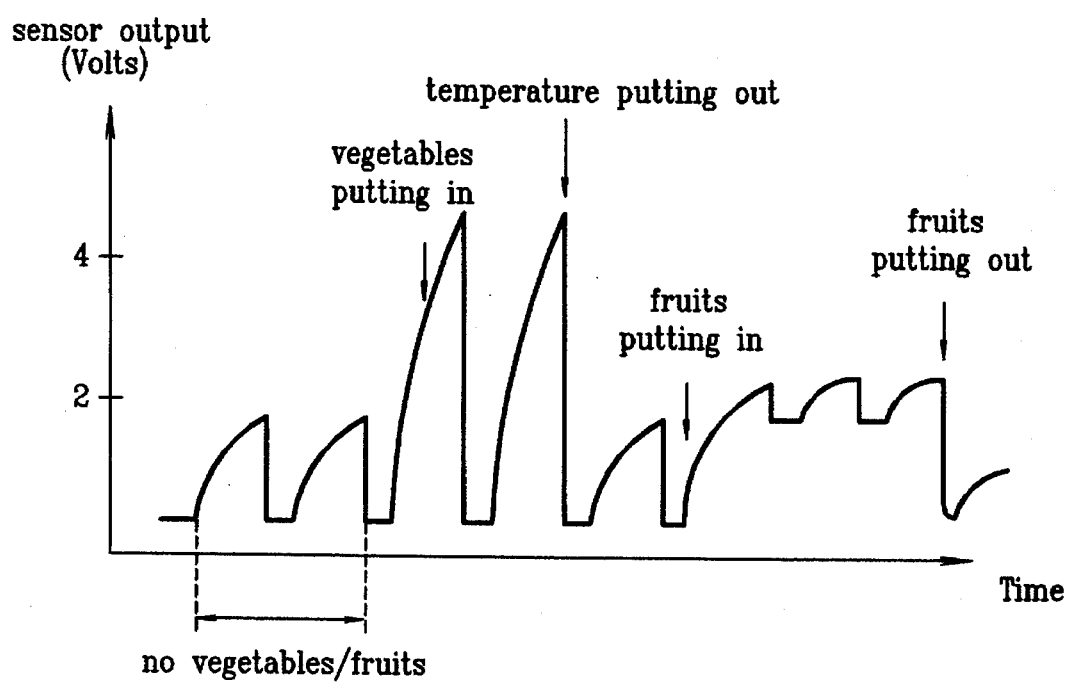

When the smellable gas output ("smell component") component of the fruits and vegetables exist in the storing compartment, the absorption reaction of the smellable component as well as the moisture is actively executed at the low temperature are as shown in FIG. 7b, so that the resistance of the sensor is abruptly decreased to significantly increase the output voltage. When heating at the temperature of a high-temperature area, the absorbed moisture is separated. Thus, the smell component is also separated. Furthermore, because the oxygen separating reaction by the reducing gases is the major factor of altering the resistance, there is a relatively smaller output variation to the smell component of the fruits or vegetables.

When the output waveform of fruits and vegetables are compared to each other, the fruits have a property of output variation being great in the high temperature area due to another reducing gas existing in the inherent smell component. Consequently, the vegetables have a greater output variation at the low temperature area, and the fruits do so at the high temperature area. Therefore, these characteristics are utilized to distinguishably sense the fruits and vegetables stored in the storing compartment.

On the other hand, in order to sense a point of putting out or removal of the fruits and vegetables from the storage compartment, a sensor signal should be restored as fast as possible when the food is put out or removed, and be less affected by the gas within the storage compartment. In this aspect of the application, it is important for an efficient operation of the storage apparatus to sense an empty state where the food is completely eliminated from the storage compartment rather than a partially stocked state where the food is partially eliminated and partially remaining therein. Accordingly, for the purpose of solving a problem that the sensor signal is not restored to the state of being empty (i.e., a signal value lacking of the gas) or a considerable time is required for the restoration, not only the distinction of the vegetables from the fruits but also the restoring characteristic is enhanced via the above-described high/low temperature operations.

The gas sensor according to the present invention as described above has the following effects. The gas sensor can efficiently control the storing apparatus by being applied to the storing apparatus such as the refrigerator. In other words, the putting in or removal of food, such as the fruits and vegetables, can be sensed in accordance with the kinds of food stored. Thus, the result of the sensing is supplied to the microprocessor which, in turn, controls the flow of cool air to force the temperature of the fruits and vegetables to reach the optimum storage temperature. Furthermore, since the storage compartment does not need to be cooled when it contains no vegetables or fruits, the flow of the cooled air is changed or the cooling of the storage compartment can be stopped to enable the storing apparatus to be efficiently operated at lower financial costs by reducing power consumption. In addition, it can be determined whether the vegetables or the fruits are put in the storage compartment to optimize the freshness by using the characteristics found from electrical measurements for the different kinds of food stored.

It will be apparent to those skilled in the art that various modifications and variations can be made in the gas sensor of the present invention without departing from the spirit or scope of the invention. Thus, it is intended that the present invention cover the modifications and variations of this invention provided they come within the scope of the appended claims and their equivalents.

What is claimed is:

1. A gas sensor for detecting a gas component from a food item comprising:

a sensing layer having an electrical resistance value that varies in accordance with a characteristic of the gas component generated from the food item to thereby sense the gas component;

first and second electrodes coupled across said sensing layer and connected to a power supply;

a heater for heating the gas sensor to a temperature of sensing operation; and a switch connected to a voltage supply for controlling whether said heater is operated in a first temperature range or in a second temperature range;

wherein the sensing layer comprises a mixture of $SnO_2$ and $WO_3$ in a predetermined ratio.

2. A gas sensor as claimed in claim 1, wherein the mixture of $SnO_2$ and $WO_3$ in the sensing layer has a ratio of 80–95 wt % of $SnO_2$ and 5–20 wt % of $WO_3$.

3. A gas sensor as claimed in claim 1, wherein the first temperature range is approximately 250°–350° C., and the second temperature range is approximately 100°–200° C.

4. A gas sensor as claimed in claim 1, further comprising:

a first set of two pins connected to the heater;

a second set of two pins connected to the first and second electrodes, respectively;

a mold resin for supporting the four pins, where each pin is separated from the other pins by a predetermined distance; and a cap formed to fit above the mold resin for protecting the sensing layer.

5. A gas sensor for detecting a gas component from a food item comprising:

a substrate;

a heater formed on a first portion of the substrate for heating the substrate to a sensing operation temperature;

first and second electrodes formed on a second portion of the substrate;

a sensing layer formed across the first and second electrodes for sensing the gas component generated from the food item, said sensing layer having an electrical resistance value between the first and second electrodes that varies in accordance with a characteristic of the gas component generated from the food item; and a switch for switching a power supply of the heater to cause the heater to be operated in a first temperature range and a second temperature range;

wherein the sensing layer comprises a mixture of $SnO_2$ and $WO_3$ in a predetermined ratio.

6. A gas sensor as claimed in claim 5, wherein the mixture of $SnO_2$ and $WO_3$ in the sensing layer has a ratio of 80–95 wt % of $SnO_2$ and 5–20 wt % of $WO_3$.

7. A gas sensor as claimed in claim 5, further comprising:

a first plurality of pins connected to the heater;

a second plurality of pins connected to the electrodes, said first and second plurality of pins supporting said substrate;

a mold resin for supporting the plurality of pins; and a cap formed to fit above the mold resin for protecting the substrate.

8. A gas sensor as claimed in claim 5, wherein the first temperature range is approximately 250°–350° C.

9. A gas sensor as claimed in claim 5, wherein the second temperature range is approximately 100°–200° C.

* * * * *